United States Patent [19]

Gandolfi et al.

[11] Patent Number: 4,839,348
[45] Date of Patent: Jun. 13, 1989

[54] 1,4-DIHYDROPYRIDINES

[75] Inventors: Carmelo A. Gandolfi; Marco Frigerio; Silvano Spinelli; Odoardo Tofanetti; Sergio Tognella, all of Milan, Italy

[73] Assignee: Boehringer Biochemia Robin S.p.A., Milan, Italy

[21] Appl. No.: 889,380

[22] Filed: Jul. 25, 1986

[30] Foreign Application Priority Data

Aug. 6, 1985 [IT] Italy ............................... 21875 A/85

[51] Int. Cl.$^4$ ................. C07D 401/04; C07D 401/12; C07D 211/86; A61K 31/455

[52] U.S. Cl. ..................... 514/89; 546/194; 546/263; 546/278; 546/275; 546/280; 546/279; 546/121; 546/285; 546/256; 546/257; 546/284; 546/281; 546/193; 546/187; 546/22; 546/321; 546/270; 544/364; 544/359; 544/333; 544/405; 514/356; 514/340; 514/341; 514/342; 514/343; 514/316; 514/318; 514/252; 514/255; 514/332; 514/333

[58] Field of Search ............... 546/321, 22, 194, 263, 546/278, 275, 280, 279, 121, 285, 256, 257, 284, 281, 193, 194, 187, 22, 321, 270; 544/364, 359, 333, 405; 514/356, 89, 340, 341, 342, 343, 316, 318, 252, 255, 332, 333, 334, 256, 300

[56] References Cited

U.S. PATENT DOCUMENTS

4,284,634  8/1981  Sato ........................... 546/321
4,532,248  7/1985  Frankowiak et al. ............. 514/240

FOREIGN PATENT DOCUMENTS

0169009  1/1986  European Pat. Off. .

OTHER PUBLICATIONS

Cupka et al., Chemical Abstracts 105:226293w.
Franckowiak et al., "The Optical Isomers . . . " European Journal of Pharmacology, 114 (1985), pp. 223–226.
Seidel, Wolfgang, "QSAR and Molecular . . . " 2nd European Seminar & Exhi. on Computer Aided Molecular Design.

Hof, R. P. et al., "Stereoselectivity at the . . . " Journal of Cardiovascular Pharmacology, 1985, pp. 689–693.
Schachtele, C. et al., "Stereoselective Inhibition . . . " Naunyn–Schmiedeberg's Arch. of Phar. 1987, pp. 340–343.
Three Onoda Papers to Wayne State University.
Honn, K. et al., "Calcium channel . . . " Proceedings of the Soc. for Exptl. Biology & Medicine 174, (1983), pp. 16–19.
Onoda, J. et al., "Cisplatin and Nefedipine . . . " Cancer Letters, 3 (1986), pp. 181–188.
Onoda, J. et al., "Calcium Channel Blockers: . . . " Hemostatic Mech & Metastasis Martinus–Nighoff, The Hague, 1984, pp. 207–226.
Onoda, J. et al., "Antithrombogenic Effects of Calcium . . . " Thromobosis Research 34; 1984, pp. 367–378.
Cupka, P. et al., "Synthesis of 2-Chloromethyl-1 . . . " Drug Res. Institute, Palarikova 31, 811 04 Bratislava, Czechoslovakia.

*Primary Examiner*—Jane T. Fan
*Attorney, Agent, or Firm*—Armstrong, Nikaido, Marmelstein & Kubovcik

[57] ABSTRACT

Dihydropyridines of formula I

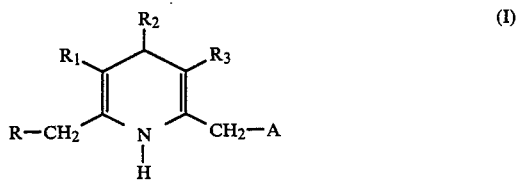

wherein R is hydrogen or lower alkyl; $R_1$ is a CN, $NO_2$, $COCH_3$, COPh group, a carboalkoxy or carboamide group; $R_2$ is an aromatic or heteroaromatic, mono- or bicyclic eventually substituted phenyl group; $R_3$ is a carboalkoxy group; while A is a halogen atom or an ammonium or phosphonium residue. The compounds I are useful as antihypertensive, antitumoral, antimetastatic, antithrombotic, and/or antiischemic agent.

6 Claims, No Drawings

1,4-DIHYDROPYRIDINES

The present invention relates to 2-(phosphonium or ammonium-methyl)-1,4-dihydropyridine salts and to their 2-halomethyl intermediates, to a method for their preparation and to pharmaceutical compositions containing them.

The compounds of the invention have the following general formula I:

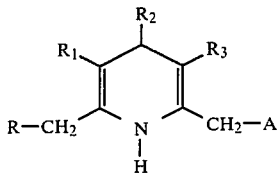

wherein

R is hydrogen or $C_1$–$C_5$ lower alkyl;

$R_1$ represents acetyl, benzoyl, cyano, nitro, an esterified carboxy group $CO_2R_4$ or an amide $-CONR_5R_6$;

$R_2$ is a member selected from the group consisting of:
 (a) a phenyl group unsubstituted or substituted by one or more $C_1$–$C_6$ alkoxy, halo-$C_1$–$C_6$ alkyl, halo-$C_1$–$C_4$ alkoxy, halogen, nitro, cyano, $C_1$–$C_6$ alkoxycarbonyl, $C_1$–$C_6$ alkylthio, $C_1$–$C_6$ alkylsulphinyl groups;
 (b) pentafluorophenyl;
 (c) α or β-naphthyl;
 (d) a five or six-membered-heterocyclic ring;
 (e) α-benzo[2,3-b]-1,4-dioxane-α-yl, or
 (f) α-benzo[3,4-c]-furoxanyl;

$R_3$ is an esterified carboxy group $CO_2R_4$;

$R_4$ is a member selected from the group consisting of a $C_1$–$C_6$ alkyl chain unsubstituted or substituted by hydroxy, amino, monoalkylamino, dialkylamino, $C_1$–$C_6$ alkoxy groups; $C_3$–$C_6$ alkenyl; an optionally substituted aryl or $C_1$–$C_4$ aralkyl group;

each of $R_5$ and $R_6$, which are the same or different, may be hydrogen, $C_1$–$C_6$ alkyl, benzyl or aryl;

A represents a chlorine, bromine or iodine atom or a phosphonium $(^{(+)}PR_7R_8R_9X^-)$ or ammonium $(^{(+)}NR_{10}R_{11}R_{12}X^-)$ group wherein each of $R_7R_8$ and $R_9$, which are the same or different, may be a $C_1$–$C_6$ lower alkyl, a substituted or unsubstituted aryl or $C_1$–$C_4$ aralkyl; $R_{10}$, $R_{11}$ and $R_{12}$ which are the same or different may be $C_1$–$C_6$ lower alkyl or one of $R_{10}$, $R_{11}$, $R_{12}$ is as defined above and the other two form a ring when taken together with the nitrogen atom to which they are linked; or one of $R_{10}$, $R_{11}$, $R_{12}$ is a bond and the other two, when taken together which the nitrogen atom to which they are linked, form a heterocyclic ring optionally substitued with a halogen, $C_1$–$C_6$ alkyl, $C_1$–$C_6$ alkoxy, a free or esterified $CO_2R_4$ group as defined, $-C\equiv N$, $-CONH_2$, a substituted or unsubstituted aryl;

$X^-$ is a pharmaceutically acceptable anion,

The optical antipodes, i.e. the enantiomers, and racemic mixture of the optical antipodes of the compounds of formula (I) are also included in the scope of the present invention.

A halo-$C_1$–$C_6$ alkyl group is preferably trihalo-$C_1$–$C_6$ alkyl, in particular trifluoromethyl.

A halo-$C_1$–$C_4$ alkoxy group is preferably difluoromethoxy.

A $C_1$–$C_6$ alkyl group is preferably methyl, ethyl, isopropyl or tert-butyl.

An aryl group is preferably phenyl.

A $C_3$–$C_6$ alkenyl is preferably allyl.

A monoalkylamino radical is preferably a methyl, ethyl, isopropyl or benzylamino group.

A dialkylamino group is preferably a dimethylamino, diethyl, benzyl- or methylamino group.

A dialkylamino group is more preferably a residue wherein the dialkyl substituent is part of a cyclic residue such as pyrrolidin-1-yl, piperidin-1-yl, pyperazin-yl, 4-substituted-pyrazin-1-yl, imidazol-1-yl, 2-alkoxycarbonyl-pyrrolidin-1-yl.

A $C_1$–$C_4$ aralkyl group is preferably benzyl.

$X^{(-)}$ is preferably $Cl^-$, $Br^-$, $I^-$, $CH_3SO_3^{(-)}$, $ClO_4^{(-)}$, $BF_4^{(-)}$, $CH_3CO_2^{(-)}$ and $(p)CH_3-C_6H_5-SO_3^{(-)}$. R is preferably hydrogen, $CONR_5R_6$ is preferably $-CONH_2$; $R_7$, $R_8$, $R_9$ are preferably the same and more preferably they are n-butyl or phenyl groups.

The preferred quaternary ammonium salts of formula $NR_{10}R_{11}R_{12}$ are 1-methylpiperidinium, triethylammonium and diaza[2,2,2]bicyclooctanium.

Preferred heteroaromatic quaternary ammonium salts are pyridinium, pyrimidinium, pyrazinium, 1-imidazolinium, oxazolium, thiazolium and pyrazolium salts. Specific examples of preferred compounds of the invention are hereinbelow reported:

2-chloromethyl-3,5-dicarboethoxy 4-(m-nitrophenyl)-6-methyl-1,4-dihydropyridine;

2-chloromethyl-3,5-dicarboethoxy-4-(m-trifluoromethylphenyl)-6-methyl-1,4-dihydropyridine;

2-chloromethyl-3,5-dicarboethoxy-4-(m-chlorophenyl)-6-methyl-1,4-dihydropyridine;

2-chloromethyl-3,5-dicarboethoxy-4-(o-methylthiophenyl)-6-methyl-1,4-dihydropyridine;

2-chloromethyl-3-carboethoxy-5-carbomethoxy-4-(m-nitrophenyl)-6-methyl-1,4-dihydropyridine;

2-chloromethyl-3-carbomethoxy-5-carboethoxy-4-(m-nitrophenyl)-6-methyl-1,4-dihydropyridine;

2-chloromethyl-3-carboethoxy-5-acetyl-4-(m-nitrophenyl)-6-methyl-1,4-dihydropyridine;

2-chloromethyl-3-carboethoxy-5-cyano-4-(m-nitrophenyl)-6-methyl-1,4-dihydropyridine;

2-iodomethyl-3,5-dicarboethoxy-4-(m-nitrophenyl)-6-methyl-1,4-dihydropyridine;

2-chloromethyl-3-carboethoxy-5-nitro-4-(m-nitrophenyl)-6-methyl-1,4-dihydropyridine;

[(6-methyl-3,5-dicarboethoxy-4-(m-nitrophenyl)-1,4-dihydropyridin-2-yl)-methyl]triethylphosphonium chloride;

[(6-methyl-3,5-dicarboethoxy-4-(m-nitrophenyl)-1,4-dihydropyridin-2-yl)-methyl]tributylphosphonium chloride;

[(6-methyl-3,5-dicarboethoxy-4-(m-nitrophenyl)-1,4-dihydropyridin-2-yl)-methyl]triphenylphosphonium chloride;

[(6-methyl-3,5-dicarboethoxy-4-(o-nitrophenyl)-1,4-dihydropyridin-2-yl)-methyl]triphenylphosphonium chloride;

[(6-methyl-3,5-dicarboethoxy-4-(o-chlorophenyl)-1,4-dihydropyridin-2-yl)-methyl]triphenylphosphonium chloride;

[(6-methyl-3-carboethoxy-5-carbomethoxy-4-(m-nitrophenyl)-1,4-dihydropyridin-2-yl)-methyl]triphenylphosphonium chloride;

[(6-methyl-3,5-dicarboethoxy-4-(m-nitrophenyl)-1,4-dihydropyridin-2-yl)-methyl]triphenylphosphonium iodide;

[(6-methyl-3-cyano-5-carboethoxy-4-(m-nitrophenyl)-1,4-dihydropyridin-2-yl)-methyl]triphenylphosphonium chloride;

1-[(6-methyl-3,5-dicarboethoxy-4-(m-nitrophenyl)-1,4-dihydropyridin-2-yl)-methyl]pyridinium chloride;

1-[(6-methyl-3,5-dicarboethoxy-4-(m-nitrophenyl)-1,4-dihydropyridin-2-yl)-methyl]-3-carbamoyl pyridinium chloride;

1-[(6-methyl-3,5-dicarboethoxy-4-(m-nitrophenyl)-1,4-dihydropyridin-2-yl)-methyl]1,4-[2,2,2]-diazabicyclooctanium chloride.

The compounds of the invention are prepared by a process comprising:
cyclization of a compound of formula II

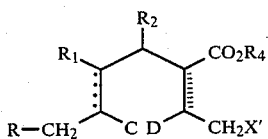

wherein R, $R_1$, $R_2$, $R_4$ are as above defined, X' is chlorine or bromine, the symbols ····· and ıııııı, which are the same or different, represent a single or a double bond and D and C are respectively $NH_2$ and OH when the symbols ·····, ıııııı are a double bond or they are =NH and =O when the symbols ·····, ıııııı are a single bond, to give a compound of formula Ia

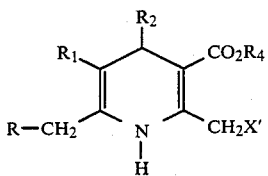

wherein R, $R_1$, $R_2$, $R_4$ and X' are as defined above.

The compounds Ia, if desired, may be optionally converted into a compound of formula Ia wherein X' is iodine or by the reaction with a phosphine ($R_7R_8R_9P$) or an amine ($R_{10}R_{11}R_{12}N$) wherein $R_7$, $R_8$, $R_9$, $R_{10}$, $R_{11}$, $R_{12}$ are as above defined to give a compound of formula I wherein A is a quaternary salt which may be optionally transformed, if desired, into another quaternary salt having a different, pharmaceutically acceptable anion.

The cyclization of a compound II may be carried out in an inert solvent either in the presence or in absence of an acid catalyst such as a hydrohalogen acid, sulfuric acid, an alkyl or an aryl sulfonic acid, formic, acetic, or trifluoroacetic acids.

Suitable solvents are $C_1$–$C_4$ lower alcohols such as methanol, ethanol, isopropanol, n-butanol and isobutanol, aromatic hydrocarbons such as benzene, toluene; linear and cyclic ether such as dimethoxyethane, tetrahydrofuran or an ester i.e. ethylacetate, as well as mixtures thereof.

The cyclization reaction is preferably carried out from −20° C. to the room temperature, preferably at about 0° C.

The reaction times range from few minutes to several hours, but usually do not exceed two hours and often a few minutes are sufficient to complete the reaction when the acid catalyst is added. The preferred amounts of the acid catalyst range from 0.01 to 0.1 molar equivalents.

The formation of a quaternary salt (I) may be carried out by reaction of a compound of formula (Ia) with either a stoichiometric amount or a small excess of a trisubstituted phosphine or amine of formula (III), in an inert solvent.

Suitable solvents are $C_1$–$C_4$ lower alcohols, i.e. methanol, ethanol; aromatic hydrocarbons such as benzene or toluene and ethers, ketones, nitriles or esters such as dimethoxyethane, tetrahydrofuran, acetone, butanone, ethylacetate, acetonitrile, as well as mixture thereof.

The reaction is preferably carried out at temperature ranging from about 0° C. to the reflux temperature of the reaction mixture, preferably from the room temperature to 80° C.

The compounds of formula II are obtained by reacting a compound of formula III

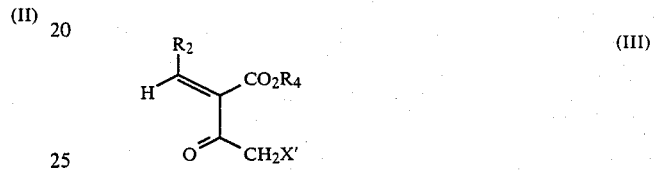

wherein $R_2$, $R_3$ and X' are as defined above, with either a stoichiometric amount of a small excess of a compound of formula IV

in an inert solvent, as above defined, such as a $C_1$–$C_4$ lower alcohol, an aromatic hydrocarbon, a linear or cyclic ether, an ester or mixtures thereof.

The reaction between compounds III and IV must be carried out under kinetic control, at a temperature ranging from little more the room temperature to the reflux temperature.

When the reaction is over, the mixture is rapidly cooled to 15÷0° C. and the product may be recovered in pure form or directly used in the process of the invention.

The reaction times range from few minutes to few hours, but usually do not exceed two hours and often a few minutes are sufficient to complete the reaction. Kinetic control means that the reaction time is strictly related to the heating temperature of the reaction mixture.

The compounds III are obtained by reaction of an aldehyde of formula V:

wherein $R_2$ is as defined above, with a 4-halo-3-oxobutanoate of formula VI:

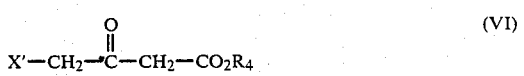

wherein $R_4$ and X' are as above defined using procedures known in the art, for example Knoevenagel reaction, i.e. refluxing the aldehyde and the β-ketoester in an inert solvent, e.g. benzene or toluene, in the presence of piperidine acetate, removing the water formed during the reaction.

Alternatively, a compound of formula III may be also prepared starting from another compound of formula III wherein X' is hydrogen, according to well known halogenation procedures of the angular methyl group (—CH$_2$X'=CH$_3$).

The compounds of formula IV are known compounds, commercially available, or easily preparable with known methods, for example by hydrogenolytic cleavage of known isoxazole precursors such as the compounds VII a-c

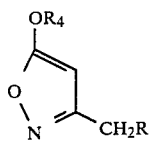
(VIIa)

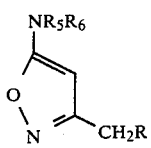
(VIIb)

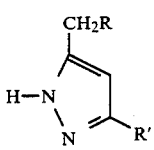
(VIIc)

wherein R, R$_4$, R$_5$, R$_6$ are as above defined and R'$_1$ is methyl or phenyl. The compounds of the invention, and particularly those wherein A is an halogen atom or a triphenylphosphonium group, may also be used as starting material for subsequent reactions such as substitution reactions or Wittig reactions with carbonyl compounds. The compounds of the invention may be therefore useful as intermediates for the preparation of the compounds disclosed in the Italian Pat. Appln. No. 21944 A/85 and 21876 A/85 in the applicant's name.

Some 2-chloromethyl-1,4-dihydropyridines of formula I wherein R is hydrogen and R$_1$ is a carboxyester group are described in the patent literature, see for example DE-A-2629842 (27.01.1977) and E.P. Appln. No. 0083315 (6.07.1983), both disclosing as starting materials 2-(or 6-)hydroxymethyl-1,4-dihydropyridines, prepared by multi-step processes; the exchange of the hydroxy group with a chlorosubstituent is carried out using conventional procedures well-known in preparative organic chemistry, for example by means of triphenylphosphine and CCl$_4$ or thionyl chloride. The crude chloromethyl derivatives are used as intermediates for the preparation of 2-cyanomethyl and of 2-(N,N-dialkylaminomethyl)-dihydropyridines. 2-Chloromethyl derivatives are also known from E.P. Appln. No. 0083315 as possible intermediates in the preparation of furo[3,4-b]dihydropyridines of formula VIII

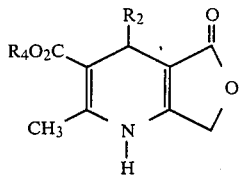
(VIII)

from an aldehyde such as R$_2$CHO, an alkyl 4-chloro-3-oxo-butanoate and an alkylaminocrotonate.

In principle, the supposed formation of 2(or 6)-halomethyl-1,4-dihydropyridines, as intermediates in the synthesis of the above-mentioned lactones, is based on the easy ring closure of alkyl-4-halo-3-oxo-butanoates and of Z-alkyl-4-halo-2,3-disubstituted-2-butanoates to furanones by alkyl halide elimination. This well-known ring closure reaction is extremely favoured by heating and sometimes may take place spontaneously after long periods at room temperature, too.

In fact, when the reaction of a compound III with a compound IV is not carried out under kinetic control in order to isolate the adduct of formula II by rapid cooling of the reaction mixture, the corresponding lactones of formula VIII are formed, as predominant reaction products.

The synthesis of lactones of formula VIII is also described in a subsequent E.P. Appln. No. 0111453 (20.06.1984) by reaction of an aldehyde with a β-aminocrotonate and 4-chloro-3-oxo-butanoate in ethanol for 30 hours. In said references, the 2 or (6)-halomethyl dihydropyridines are cited only as intermediates and no therapeutic activity is reported.

The compounds of the invention show an antagonistic properties "in vitro" and antihypertensive activity "in vivo" after oral administration.

For example the compounds of the invention are able to inhibit "in vitro" the contractions induced by CaCl$_2$, in K$^+$-depolarized aorta strips, when tested according to the Godfraind's procedure (T. Godfraind et al., Arch. Intern. Pharmacodyn. 172, 235, 1968), in comparison with nifedipine, a known Ca-antagonist drug, as reference compound.

The compounds of the invention exhibit ID$_{50}$ values ranging from $1.5 \cdot 10^{-8}$ and $3 \cdot 10^{-9}$, in comparison with an ID$_{50}$ of $2.7 \cdot 10^{-8}$ for the reference substance.

The antihypertensive activity of the compounds of the invention was investigated in spontaneously hypertensive rats (SH rats) measuring the decrease of the mean blood pressure after oral administration.

Many compounds of the invention, when administered at a dose level lower than 1/10 of their LD$_{50}$, show a 15% decrease of the mean blood pressure (mean BP) with respect to the basal value, at least. This 15% decrease of the mean BP is generally considered to be a predictive proof for a significant cardiovascular activity.

Receptorial binding studies on cerebral rat membranes show that the quaternary ammonium salts are endowed with good affinities. Said compounds, when administered orally to SH rats, don't induce a remarkable antihypertensive effect, but a decrease of the heart rate is observed.

Some compounds of the invention were tested in order to assess their potential as inhibitors of the growth of tumoral cells in vitro and in particular the phosphonium salts show inhibitory activity at a final dilution of 1-10 μg/ml in the growth medium.

Representative compounds of the invention are 2-chloromethyl-3,5-dicarboethoxy-4-(m-nitrophenyl)-6-methyl-1,4-dihydropyridines, for which a decrease in the mean BP of 45 mmHg is observed after oral administration to conscious SH rates at a dosage of 10 mg/kg ($DL_{50} > 1$ g in normal rats by oral route), and [3,5-dicarboethoxy-4-(m-nitrophenyl)-6-methyl-1,4-dihydropyridine-2-yl]methyl-triphenylphosphonium chloride.

For the latter compound, a decrease of 56 mmHg in the mean BP is observed after oral administration of 3 mg/kg to SH rats ($LD_{50} > 1000$ by oral route).

The compounds of the invention are also able to protect cellular membranes from oxidative injuries. A decreased production of malondialdehyde is observed after incubation of rat erithrocyte membranes with the compounds of the invention (test of M. Aishita et al., Arch. Intern. Pharmacodyn., 261, 316, 1983).

Sudden death of mice, induced by bolus administration of a mixture of collagene and ADP mixture, is prevented by previous oral administration of the compounds of the invention.

The compounds of the invention ae consequently able to interact with intracellular availability of calcium ions and they are therefore useful for the regulation of metabolic processes involved in the contraction of smooth vascular muscles.

The compounds of the general formula I are therefore useful as vasodilators, antihypertensive agents as well as antithrombotic and antimetastatic drugs. To obtain the desired therapeutic effect, the compounds of the invention of the formula I may be administered to the patient in different ways, alone or in pharmaceutical preparation by oral or parenteral route, i.e. intravenously or intramuscularly. A pharmaceutical composition suitable for this purpose can be prepared according to the known techniques, as described for instance in "Remington's Pharmaceutical Sciences Handbook", Hack Publishing Company, U.S.A.

The administered amounts vary according to the gravity of the treated disease and to the administration route. If administered orally, the quantity of the active principle administered varies from 0.01 mg/kg to 10 mg/kg of the patient's body weight pro die. If administered parenterally, the amount of active principle varies from 0.001 mg/kg to 5 mg/kg of patient's body weight pro die and it is preferably comprised between 0.01 mg/kg and 2 mg/kg of patient's body weight pro die.

A single dose for oral administration may contain for example from 0.05 to 100 mg of active principle. A single dose for parenteral administration may contain, for example, from 0.05 to 70 mg of active principle.

The compounds of the invention, because of their long lasting effect, may be administered once or twice a day; however repeated daily administrations could be—at least in some cases—desirable and may vary according to the patient's conditions or the administration route. The word "patient" means not only human beings, but generally warm-blooded animals.

For the oral administration, the compound may be formulated in solid or liquid preparations such as capsules, pills, tablets, powders, solutions, suspensions or emulsions. The unit dosage form may be the hard or soft gelatine capsule containing for instance lubricants and inert excipients such as lactose, saccharose or starch. Alternatively, the compounds of the invention may be administered as tablets, on carriers such as lactose, saccharose or starch in combination with binders such as starch itself or gelatin, disintegrating agents such as potato starch, or alginic acid, and lubricants such as stearic acid and magnesium stearate.

For parenteral administration the compounds of the invention may be administered in injectable forms, dissolved or suspended in pharmaceutically acceptable diluents, with a pharmaceutical carrier such as a sterile liquid such as water or an oil, with or without the addition of other pharmaceutically acceptable excipients. Oils which may be used in said preparations are of mineral, vegetal, animal or synthetic kind. Generally, as a carrier for injectable solutions the following substances may be used: water, salts, aqueous solutions, dextrose or other sugars aqueous solutions, ethanol, glycols such as propylenglycol and polyethylenglycols.

For the rectal administration, the compounds may be formulated in forms of suppositories, mixed with conventional vehicles such as, for example, cocoa butter, wax, polyvinylpyrrolidone or polyoxyethyleneglycols, or derivatives thereof.

The administration route generally preferred is the oral route, while the preferred pharmaceutical formulations are capsules.

The invention is illustrated by the following non limitative examples, wherein the abbreviation $Et_2O$, EtOH, AcOEt, $CH_3CN$, MeOH, refer to dithylether, ethanol, ethylacetate, acetonitrile, methanol, respectively.

EXAMPLE 1

A mixture of ethyl 4-chloroacetate (108 g), m-nitrobenzaldehyde (100 g), acetic acid (7.2 ml) and piperidine (2.6 ml) in benzene (800 ml) is heated to the reflux temperature, in a Dean-Stark apparatus provided with a water separator, for two hours, then it is cooled to room temperature, washed with water (5×50 ml), dried on $Na_2SO_4$ and evaporated to dryness. The residue is dissolved in $Et_2O$ (200 ml) to give 85 g of ethyl 2-(m-nitrophenylmethylen)-4-chloro-3-oxo-butanoate, m.p. 108°–111° C.

EXAMPLE 2

Using in the procedure described in Example 1 a substituted-benzaldehyde and an alkyl 2-(substituted-phenyl)-3-oxo-butanoate the compounds listed hereinbelow are prepared:

| $R_2$ | $R_4$ | m.p. (°C.) |
|---|---|---|
| $C_6H_5$ | Et | oil |
| o-Cl—$C_6H_4$ | Et | oil |
| m-Cl—$C_6H_4$ | Et | oil |
| p-F—$C_6H_4$ | Et | oil |
| o-$NO_2$—$C_6H_4$ | Et | 112–116 |
| p-$NO_2$—$C_6H_4$ | Et | 89–91 |
| m-$NO_2$—$C_6H_4$ | Me | 148–150 |
| m-$NO_2$—$C_6H_4$ | t-But | 88–90 |
| o-$CF_3$—$C_6H_4$ | Et | oil |
| m-$CF_3$—$C_6H_4$ | Et | oil |
| m-$OCH_3$—$C_6H_4$ | Et | oil |
| o-$SCH_3$—$C_6H_4$ | Et | oil |
| β-pyridyl | Et | oil |
| α-thienyl | Et | oil |

EXAMPLE 3

A solution of ethyl 2-(m-chlorophenylmethylen)-4-chloro-3-oxobutanoate (5 g) and ethyl-3-aminocrotonate (2.3 g) in EtOH (50 ml) is stirred at room temperature for four hours, then it is evaporated at reduced pressure, the residue dissolved in Et$_2$O (70 ml) washed with water (3×20 ml), dried on Na$_2$SO$_4$ and purified by column-chromatography on silica gel (120 g; eluent hexane/AcOEt 60/40) to give 4.2 g of 2-amino-7-chloro-3,5-dicarboethoxy-6-oxo-4-(m-chlorophenyl)-2-heptene as an oil.

NMR (CDCl$_3$) δ (TMS): 1.00–1.30 (6H, t); 2.20–3.80 (7H, m); 4.00–4.20 (4H, q); 7.00–7.30 (4H, m); 7.60–8.00 (2H, m; exchanges with D$_2$O).

EXAMPLE 4

A solution of ethyl 2-(m-trifluoromethylphenylphenylmethyl)-4-chloro-3-oxobutanoate (8 g) and ethyl 3-aminocrotonate (3.4 g) in EtOH (80 ml) is heated to reflux temperature for 10 minutes, then it is cooled at room temperature and after usual work-up the residue is purified by column-chromatography on silica-gel (300 g, eluent Et$_2$O/isopropylether 50/50) to give 6 g of 2-amino-7-chloro-3,5-dicarboethoxy-4-(m-trifluoromethylphenyl)-6-oxo-2-heptene as an oil.

NMR (CDCl$_3$) δ (THS): 1.10–1.30 (6H t); 2.30–3.80 (7H, m); 3.90–4.20 (4H, q); 7.00–8.10 (6H, m; partially exchanges with D$_2$O).

EXAMPLE 5

Using in the procedure described in Examples 3–4 a suitable alkyl 2-(substituted methylene)-4-chloro-3-oxobutanoate and an alkyl 3-aminocrotonate the following 2-amino-7-chloro-6-oxo-2-heptene derivatives are prepared:
3-carboethoxy-5-carbomethoxy-4-(m-nitrophenyl);
3,5-dicarboethoxy-4-(m-nitrophenyl);
3-carboethoxy-5-carboisopropoxy-4-(m-nitrophenyl);
3,5-dicarboethoxy-4-phenyl;
3,5-dicarboethoxy-4-(p-fluorophenyl);
3-carboethoxy-5-carbomethoxy-4-(m-trifluoromethylphenyl).

EXAMPLE 6

A solution of 2-amino-7-chloro-3-carboethoxy-5-carbomethoxy-4-(m-trifluoromethylphenyl)-6-oxo-2-heptene (5 g) and aqueous concentrated HCl (0.2 ml) in EtOH (50 ml) is stirred at 0° C. for 2 hours then it is neutralized with a drop of a saturated NaHCO$_3$ solution and evaporated to dryness. The residue is dissolved in AcOEt (50 ml), washed with water (3×15 ml), dried on Na$_2$SO$_4$ and concentrated in vacuum. The residue is dissolved in Et$_2$O/diisopropylether to give 3.6 g of 2-chloromethyl-3-carboethoxy-5-carbomethoxy-4-(m-trifluoromethylphenyl)-6-methyl-1,4-dihydropyridine, m.p. 115°–116° C.

EXAMPLE 7

A mixture of ethyl 2-(m-nitrophenylmethylene)-4-chloro-3-oxobutanoate (80 g) and methyl 3-aminocrotonate (32.7 g) in EtOH (800 ml) is heated to reflux temperature for 15 minutes, then, without isolating the formed intermediate, 2-amino-7-chloro-3-carboethoxy-5-carbomethoxy-4-(m-nitrophenyl)-6-oxo-2-heptene, the mixture is cooled at 0° C. and acidified with aqueous concentrated HCl (3 ml). After two hours the reaction mixture is neutralized with a few drops of a saturated NaHCO$_3$ solution and evaporated to dryness. The residue is dissolved in AcOEt (400 ml), washed with water (4×50 ml), dried on Na$_2$SO$_4$ and concentrated in vacuum. The residue is dissolved in Et$_2$O to give 80 g of 2-chloromethyl-3-carboethoxy-5-carbomethoxy-4-(m-nitrophenyl)-6-methyl-1,4-dihydropyridine (m.p. 119°–120° C.).

EXAMPLE 8

Using in the procedure described in Example 6 a suitable 2-amino-6-oxo-2-heptene or in the procedure described in Example 7 an enamine selected from alkyl 3-aminocrotonate, 3-aminocrotononitrile, 2-amino-3-nitro-2-propene, 4-amino-3-penten-2-one, 3-amino-1-phenyl-2-buten-1-one and a suitable alkyl 2-(substituted methylene)-4-chloro-3-oxo-butanoate, the following 1,4-dihydropyridines are obtained:

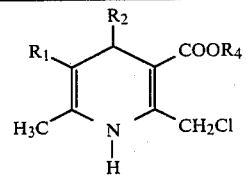

| R$_1$ | R$_2$ | R$_4$ | M.p. (°C.) |
|---|---|---|---|
| CO$_2$Et | m-NO$_2$—C$_6$H$_4$ | Et | 129–131 |
| CO$_2$Et | o-NO$_2$—C$_6$H$_4$ | Et | 115–116 |
| CO$_2$Me | m-NO$_2$—C$_6$H$_4$ | Me | oil |
| CO$_2$C$_3$H$_7$—i | m-NO$_2$—C$_6$H$_4$ | Et | 99–102 |
| CO$_2$Me | m-NO$_2$—C$_6$H$_4$ | C$_4$H$_9$—t | oil |
| CO$_2$C$_4$H$_9$—t | m-NO$_2$—C$_6$H$_4$ | Et | 80–84 |
| CO$_2$Me | p-NO$_2$—C$_6$H$_4$ | Et | 135–137 |
| CO$_2$CH$_2$CH$_2$N—(CH$_3$)CH$_2$C$_6$H$_5$ | m-NO$_2$C$_6$H$_4$ | Et | oil |
| CO$_2$Me | C$_6$H$_5$ | Et | 82–85 |
| CO$_2$Me | o-CF$_3$—C$_6$H$_4$ | Et | oil |
| CO$_2$Et | o-CF$_3$—C$_6$H$_4$ | Et | oil |
| CO$_2$Me | o-Cl—C$_6$H$_4$ | Et | oil |
| CO$_2$Et | o-Cl—C$_6$H$_4$ | Et | 50–52 |
| CO$_2$Me | m-Cl—C$_6$H$_4$ | Et | 109–111 |
| CO$_2$Et | o-SCH$_3$—C$_6$H$_4$ | Et | oil |
| CO$_2$Me | m-OCH$_3$—C$_6$H$_4$ | Et | 136–138 |
| CO$_2$Me | p-F—C$_6$H$_4$ | Et | 115–117 |
| CN | m-NO$_2$—C$_6$H$_4$ | Et | 151–152 |

-continued

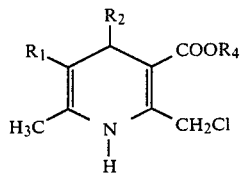

| R₁ | R₂ | R₄ | M.p. (°C.) |
|---|---|---|---|
| NO₂ | m-NO₂—C₆H₄ | Et | 158–160 |
| COCH₃ | m-NO₂—C₆H₄ | Et | oil |
| COC₆H₅ | m-NO₂—C₆H₄ | Et | oil |
| CO₂Et | β-pyridyl | Et | oil |
| CO₂Et | α-thienyl | Et | oil |
| CO₂CH(CH₃)φ | m-NO₂—C₆H₄ | Et | oil |

EXAMPLE 9

A mixture of 2-chlorometyl-3,5-dicarboethoxy-4-(m-nitrophenyl)-6-methyl-1,4-dihydropyridine (0.5 g) and potassium iodide (1 g) in acetone (5 ml) is stirred at room temperature for 24 hours, then it is filtered, concentrated under reduced pressure and the residue purified by column chromatography on silica gel (20 g, eluent: hexane/AcOEt 80/20) to give 0.22 g of 2-iodomethyl-3,5-dicarboethoxy-4-(m-nitrophenyl)-6-methyl-1,4-dihydropyridine as an oil.

NMR (CDCl₃) δ (THS): 1.10–1.30 (6H, t); 2.20 (3H, s);
3.90–4.20 (4H, q); 5.10 (1H, m); 5.20–5.30 (2H, dd); 6.70 (1H, m); 7.10–8.10 (4H, m).

EXAMPLE 10

A mixture of 2-chloromethyl-3,5-dicarboethoxy-4-(m-nitrophenyl)-6-methyl-1,4-dihydropyridine (6 g) and triphenylphosphine (4 g) in CH₃CN (60 ml) is heated to reflux temperature for six hours, then it is evaporated in vacuum and the residue crystallized from EtOH to give 6.5 g of [6-methyl-3,5-dicarboethoxy-4-(m-nitrophenyl)-1,4-dihydropyridin-2-yl]methyltriphenylphosphonium chloride, m.p. 225°–227° C.

EXAMPLE 11

Using in the procedure of Example 6 a suitable 2-halomethyl-1,4-dihydropyridine and a phosphine selected in the group of triphenylphosphine, tributylphosphine and triethylphosphine, the following compounds are obtained:

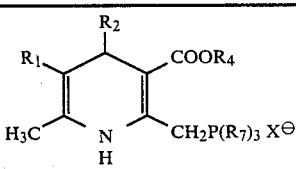

| R₁ | R₂ | R₄ | R₇ | X | M.p. (°C.) |
|---|---|---|---|---|---|
| CO₂Et | m-NO₂—C₆H₄ | Et | n-C₄H₉ | Cl | 90–92 |
| CO₂Et | m-NO₂—C₆H₄ | Et | n-C₄H₉ | I | |
| CO₂Me | m-NO₂—C₆H₄ | Et | C₆H₅ | Cl | 196–199 |
| CO₂Me | m-NO₂—C₆H₄ | Et | n-C₄H₉ | Cl | |
| CO₂Me | o-Cl—C₆H₄ | Et | C₆H₅ | I | |
| CO₂Et | o-CF₃—C₆H₄ | Et | n-C₄H₉ | Cl | |
| CN | m-NO₂—C₆H₄ | Et | C₆H₅ | Cl | 173–176 |
| NO₂ | m-NO₂—C₆H₄ | Et | n-C₄H₉ | Cl | |
| CO₂Et | β-pyridyl | Et | n-C₄H₉ | Cl | |
| CO₂Et | α-thienyl | Et | n-C₄H₉ | Cl | |

-continued

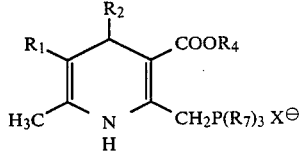

| R₁ | R₂ | R₄ | R₇ | X | M.p. (°C.) |
|---|---|---|---|---|---|
| CO₂Et | m-NO₂—C₆H₄ | Et | C₂H₅ | Cl | |

EXAMPLE 12

A solution of 2-chloromethyl-3,5-dicarboethoxy-4-(m-nitrophyenyl)-6-methyl-1,4-dihydropyridine (5 g) and pyridine (15 ml) in acetone (20 ml) is heated to reflux temperature for six hours, then it is cooled at room temperature, stirred for two hours and the formed crystaline precipitate is filtered off. Recrystallization from MeOH/acetone (70/30) gives 4.9 g of 1-[6-methyl-3,5-dicarboethoxy-4-(m-nitrophenyl)-1,4-dihydropyridin-2-yl]methyl-pyridinium chloride, m.p. 182°–184° C.

EXAMPLE 13

Using in the above described procedure a suitable tertiary amine or heteroaromatic aza compound and a halomethyl-1,4-dihydropyridine, the following compounds are obtained:
1-[6-methyl-3,5-dicarboethoxy-4-(m-nitrophenyl)-1,4-dihydropyridin-2-yl]methyl-3-carbamoylpyridinium chloride, m.p. 210°–211° C.;
[6-methyl-3,5-dicarboethoxy-4-(m-nitrophenyl)-1,4-dihydropyridin-2-yl]methyltributylammonium chloride, m.p. 118°–120° C.;
1-[6-methyl-3-carboethoxy-5-carbomethoxy-4-(o-chlorophenyl)-1,4-dihydropyridin-2-yl]methyl-pyridinium chloride;
1-[6-methyl-3,5-dicarboethoxy-4-phenyl-1,4-dihydropyridin-2-yl]methyl-pyridinium iodide;
1-[6-methyl-3,5-dicarboethoxy-4-(m-trifluoromethylphenyl)-1,4-dihydropyridin-2-yl]methyl-3-carboethoxypyridinium chloride;
1-[6-methyl-3-carboethoxy-5-cyano-4-(m-nitrophenyl)-1,4-dihydropyridin-2-yl]methyl-pyridinium chloride;
1-[6-methyl-3,5-dicarboethoxy-4-(m-nitrophenyl)-1,4-dihydropyridin-2-yl]-1,4-[2,2,2]diazabicyclooctanium chloride trihydrate, m.p. 133°–135° C.;
1-[6-methyl-3,5-dicarboethoxy-4-(α-thienyl)-1,4-dihydropyridin-2-yl]methyl-triethylammonium chloride;

1-[6-methyl-3,5-dicarboethoxy-4-(o-methylthiophenyl)-1,4-dihydropyridin-2-yl]methyl-3-methylimidazolium chloride.

We claim:

1. A compound of the formula I

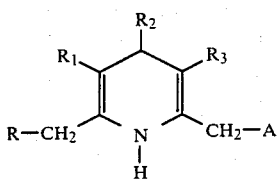

wherein

R is hydrogen or $C_1$–$C_5$ lower alkyl;

$R_1$ represents acetyl, benzoyl, cyano, nitro, an esterified carboxy group $CO_2R_4$ or an amide —$CONR_5R_6$;

$R_2$ is a member selected from the group consisting of:
(a) a phenyl group unsubstituted or substituted by one or more $C_1$–$C_6$ alkoxy, halo-$C_1$–$C_6$ alkyl, halo-$C_1$–$C_4$ alkoxy, halogen, nitro, cyano, $C_1$–$C_6$ alkoxycarbonyl, $C_1$–$C_6$ alkylthio, $C_1$–$C_6$ alkylsulphinyl groups;
(b) pentafluorophenyl;
(c) α- or β-naphthyl;
(d) 2-thienyl or β-pyridyl;
(e) α-benzo[2,3-b]-1,4-dioxane-α-yl, or
(f) α-benzo[3,4-c]-furoxanyl;

$R_3$ is an esterified carboxy group $CO_2R_4$;

$R_4$ is a member selected from the group consisting of a $C_1$–$C_6$ alkyl chain unsubstituted or substituted by hydroxy, amino, benzylamino, alkylamino selected from the group consisting of methylamino, ethylamino and isopropylamino, dialkylamino selected from the group consisting of dimethylamino and diethylamino, heterocycle selected from the group consisting of pyrrolidin-1-yl, piperidin-1-yl, piperazin-1-yl, imidazol-1-yl, and 2-alkoxycarbonyl-pyrrolidin-1-yl, and $C_1$–$C_6$ alkoxy groups; $C_3$–$C_6$ alkenyl; phenyl or ($C_1$–$C_4$ alkyl) phenyl;

each of $R_5$ and $R_6$, which are the same or different, may be hydrogen, $C_1$–$C_6$ alkyl, benzyl or phenyl;

A represents a phosphonium group or a quaternary ammonium grop, said phosphonium group having the formula $^{(+)}PR_7R_8R_9X^-$ wherein each of $R_7$, $R_8$ and $R_9$, which are the same or different, may be a $C_1$–$C_6$ lower alkyl, phenyl, or ($C_1$–$C_4$alkyl) phenyl; said quaternary ammonium group being selected from the formulas IX, X and XI:

$$^{(+)}NR_{10}R_{11}R_{12}X^-  \quad (IX)$$

wherein each of $R_{10}$, $R_{11}$ and $R_{12}$, which are the same or different, is a $C_1$–$C_6$ lower alkyl;

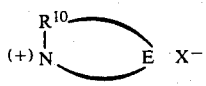

wherein $R^{10}$ is a $C_1$–$C_6$ lower alkyl, and E is a group which forms with the quaternary nitrogen atom a piperidinium ring;

wherein G is a group which forms with the quaternary nitrogen atom an unsubstituted or a substituted heterocyclic ring selected from the group consisting of pyridinium, pyrimidinium, pyrazinium, 1-imidazolinium, oxazolium, thiazolium, pyrazolium, and diaza[2,2,2-]bicyclooctanium, wherein said substituted heterocyclic ring carries at least one substituent selected from the group consisting of a halogen, $C_1$–$C_6$ alkyl, $C_1$–$C_6$ alkoxy, a free or esterified $CO_2R_4$ group as above defined, —C≡N, —$CONH_2$, and phenyl;

$X^-$ is a pharmaceutically acceptable anion, a salt, enantiomer, or diastereoisomer thereof.

2. A compound according to claim 1, wherein A is a phosphonium group.

3. A compound according to claim 1, wherein A is a quaternary ammonium group.

4. A compound according to any one of the preceding claims, wherein R is hydrogen, and $R_2$ is a phenyl group unsubstituted or substituted by one or more $C_1$–$C_6$ alkoxy, halo-$C_1$–$C_6$ alkyl, halo-$C_1$–$C_4$ alkoxy, halogen, nitro, cyano, $C_1$–$C_6$ alkoxycarbonyl, $C_1$–$C_6$ alkylthio, $C_1$–$C_6$ alkylsulphinyl groups.

5. A compound according to claim 1, selected from the group consisting of:

[(6-methyl-3,5-dicarboethoxy-4-(m-nitrophenyl)-1,4-dihydropyridin-2-yl)-methyl]triethylphosphonium chloride;

[(6-methyl-3,5-dicarboethoxy-4-(m-nitrophenyl)-1,4-dihydropyridin-2-yl)-methyl]tributylphosphonium chloride;

[(6-methyl-3,5-dicarboethoxy-4-(m-nitrophenyl)-1,4-dihydropyridin-2-yl)-methyl]triphenylphosphonium chloride;

[(6-methyl-3,5-dicarboethoxy-4-(o-nitrophenyl)-1,4-dihydropyridin-2-yl)-methyl]triphenylphosphonium chloride;

[(6-methyl-3,5-dicarboethoxy-4-(o-chlorophenyl)-1,4-dihydropyridin-2-yl)-methyl]triphenylphosphonium chloride;

[(6-methyl-3-carboethoxy-5-carbomethoxy-4-(m-nitrophenyl)-1,4-dihyropyridin-2-yl)-methyl]triphenylphosphonium chloride;

[(6-methyl-3,5-dicarboethoxy-4-(m-nitrophenyl)-1,4-dihydropyridin-2-yl)-methyl]triphenylphosphonium iodide;

[(6-methyl-3-cyano-5-carboethoxy-4-(m-nitrophenyl)-1,4-dihydropyridin-2-yl)-methyl]triphenylphosphonium chloride;

1-[(6-methyl-3,5-dicarboethoxy-4-(m-nitrophenyl)-1,4-dihydropyridin-2-yl)-methyl]pyridinium chloride;

1-[(6-methyl-3,5-dicarboethoxy-4-(m-nitrophenyl)-1,4-dihydropyridin-2-yl)-methyl]-3-carbamoyl pyridinium chloride;

1-[(6-methyl-3,5-dicarboethoxy-4-(m-nitrophenyl)-1,4-dihydropyridin-2-yl)-methyl]1,4-[2,2,2]-diazabicyclooctanium chloride.

6. A pharmaceutical composition for antihypertensive, antithrombotic, and antiischemic therapy, said composition comprising a therapeutically effective amount of a compound of claim 1, 2, 3, 5 or 6 and a pharmaceutically acceptable carrier.

* * * * *